US011553838B2

(12) United States Patent
Arai et al.

(10) Patent No.: US 11,553,838 B2
(45) Date of Patent: Jan. 17, 2023

(54) ENDOSCOPE AND ARM SYSTEM

(71) Applicant: SONY CORPORATION, Tokyo (JP)

(72) Inventors: Jun Arai, Tokyo (JP); Yohei Kuroda, Tokyo (JP); Masaru Usui, Tokyo (JP); Tetsuharu Fukushima, Tokyo (JP); Daisuke Nagao, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 185 days.

(21) Appl. No.: 16/980,011

(22) PCT Filed: Feb. 4, 2019

(86) PCT No.: PCT/JP2019/003917
§ 371 (c)(1),
(2) Date: Sep. 11, 2020

(87) PCT Pub. No.: WO2019/181242
PCT Pub. Date: Sep. 26, 2019

(65) Prior Publication Data
US 2021/0007593 A1 Jan. 14, 2021

(30) Foreign Application Priority Data
Mar. 20, 2018 (JP) .............................. JP2018-052295

(51) Int. Cl.
*A61B 1/07* (2006.01)
*A61B 1/00* (2006.01)
*A61B 1/06* (2006.01)

(52) U.S. Cl.
CPC ............ *A61B 1/07* (2013.01); *A61B 1/00117* (2013.01); *A61B 1/00126* (2013.01); *A61B 1/00149* (2013.01); *A61B 1/0661* (2013.01)

(58) Field of Classification Search
CPC . A61B 1/00117; A61B 1/0126; A61B 1/0661; A61B 1/0669; A61B 1/07
(Continued)

(56) References Cited

U.S. PATENT DOCUMENTS 5,588,950 A * 12/1996 Sano .................. A61B 1/00126
600/178
5,621,830 A * 4/1997 Lucey .................... A61B 1/317
600/137
(Continued)

FOREIGN PATENT DOCUMENTS

CN 104168812 A 11/2014
EP 2823748 A1 1/2015
(Continued)

OTHER PUBLICATIONS

International Search Report and Written Opinion of PCT Application No. PCT/JP2019/003917, dated May 7, 2019, 10 pages of ISRWO.

*Primary Examiner* — Aaron B Fairchild
(74) *Attorney, Agent, or Firm* — Chip Law Group

(57) ABSTRACT

There is provided an endoscope including a main body including a coupler to which a cable is attached, a tubular section having a tubular form, a reflector having a reflection surface that reflects light introduced from the coupler to inside of the main body and introduces the light to inside of the tubular section, a first optical system that transmits the light introduced by the reflector to the inside of the tubular section to a front-end portion of the tubular section and irradiates a subject with the light from the front-end portion, and a second optical system that transmits reflected light of the subject from the front-end portion of the tubular section to the main body side. The coupler is provided to be rotatable in the main body around a central axis of the tubular section with respect to another portion. The cable is coupled to a light source.

13 Claims, 9 Drawing Sheets

(58) Field of Classification Search
USPC .......................................................... 600/137
See application file for complete search history.

(56) References Cited

U.S. PATENT DOCUMENTS

| | | |
|---|---|---|
| 6,120,433 A | 9/2000 | Mizuno et al. |
| 2014/0371602 A1 | 12/2014 | Ito et al. |
| 2017/0135563 A1 | 5/2017 | Uemori |

FOREIGN PATENT DOCUMENTS

| | | | |
|---|---|---|---|
| JP | 08-117238 A | 5/1996 | |
| JP | 2000-316794 A | 11/2000 | |
| JP | 2000316794 * | 11/2000 | ............... A61B 1/00 |
| JP | 2003-279862 A | 10/2003 | |
| JP | 2016-087141 A | 5/2016 | |
| WO | 2013/133340 A1 | 9/2013 | |
| WO | 2016/072059 A1 | 5/2016 | |

* cited by examiner

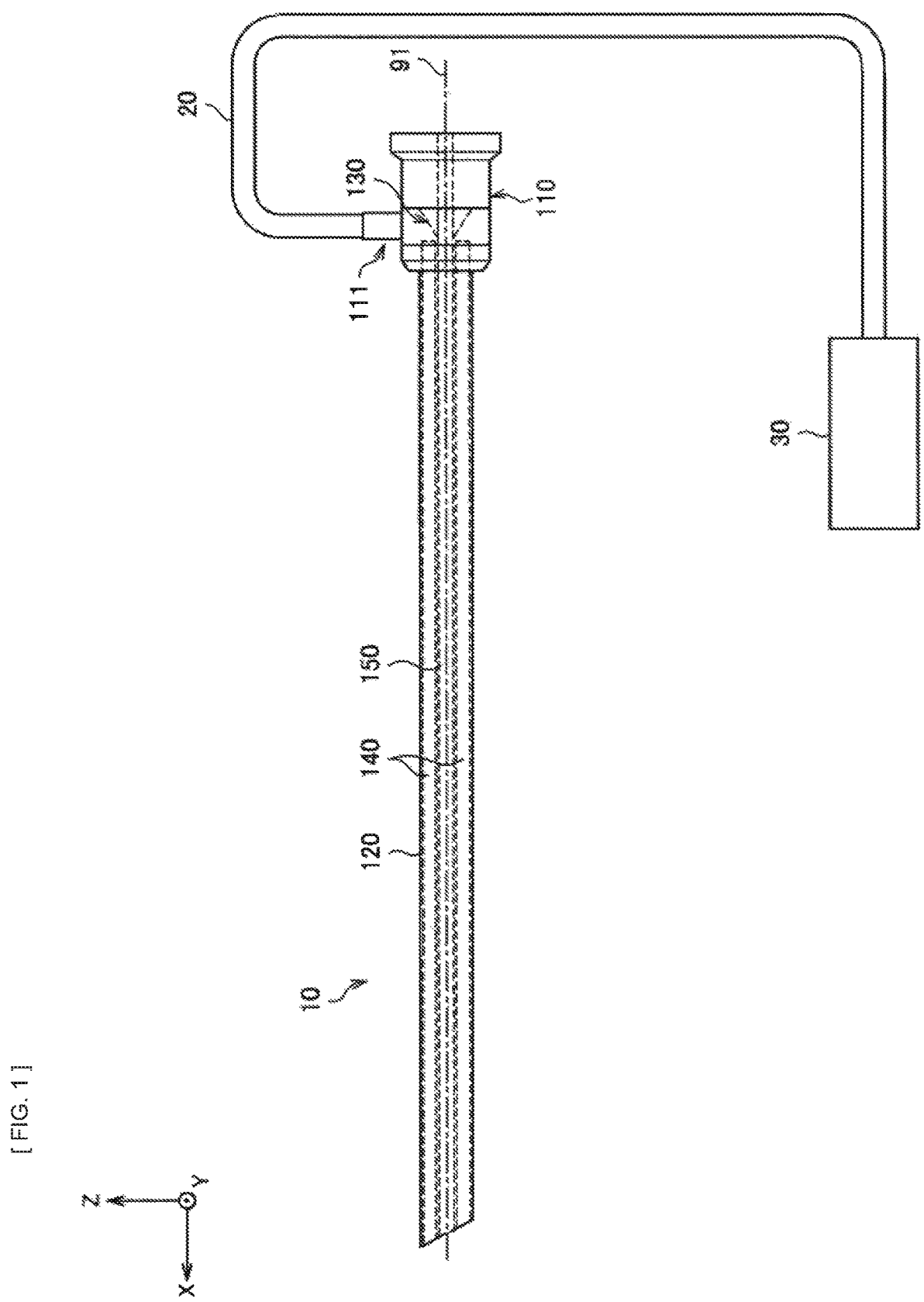

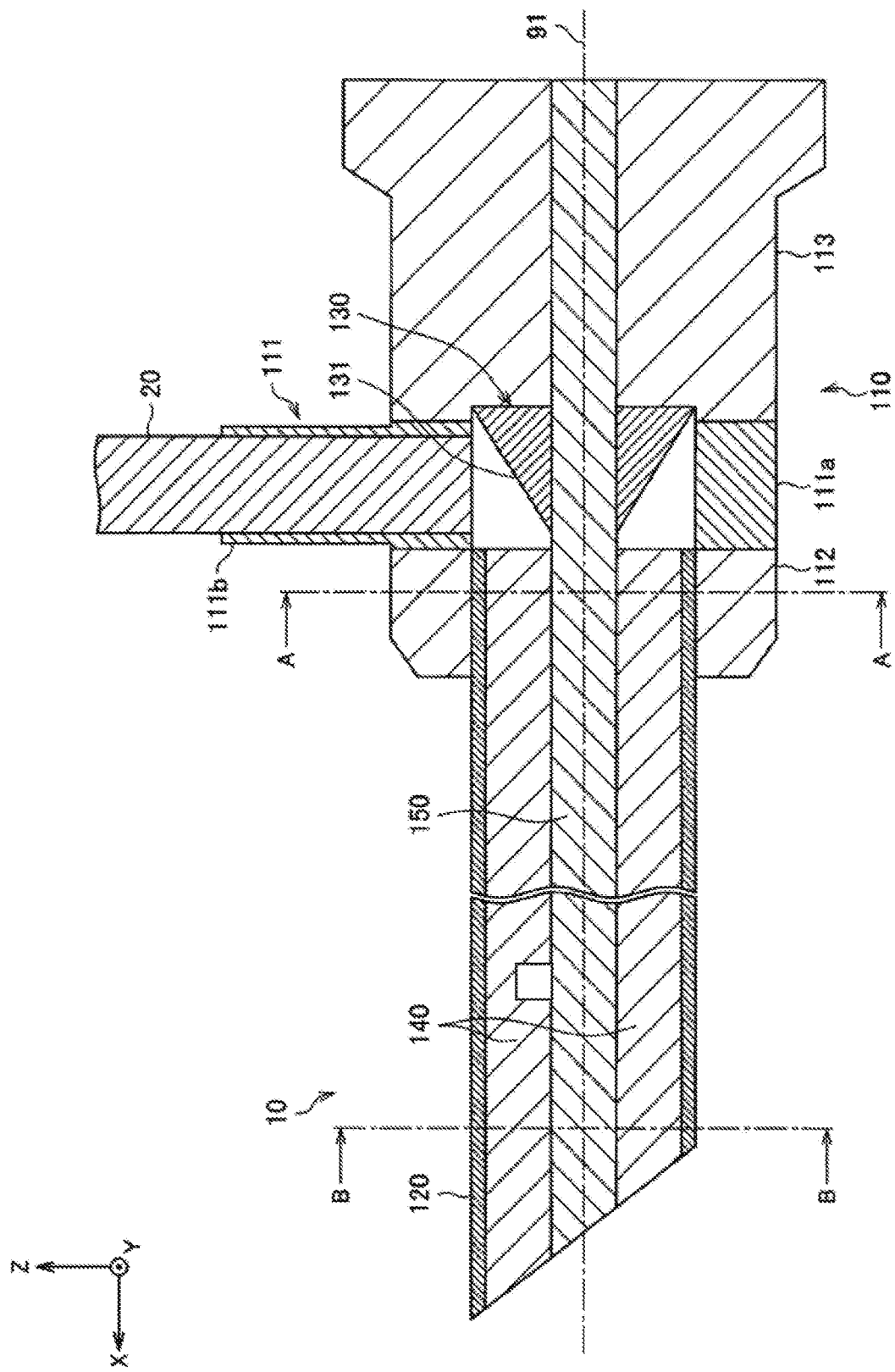
[FIG. 2]

[FIG. 3]
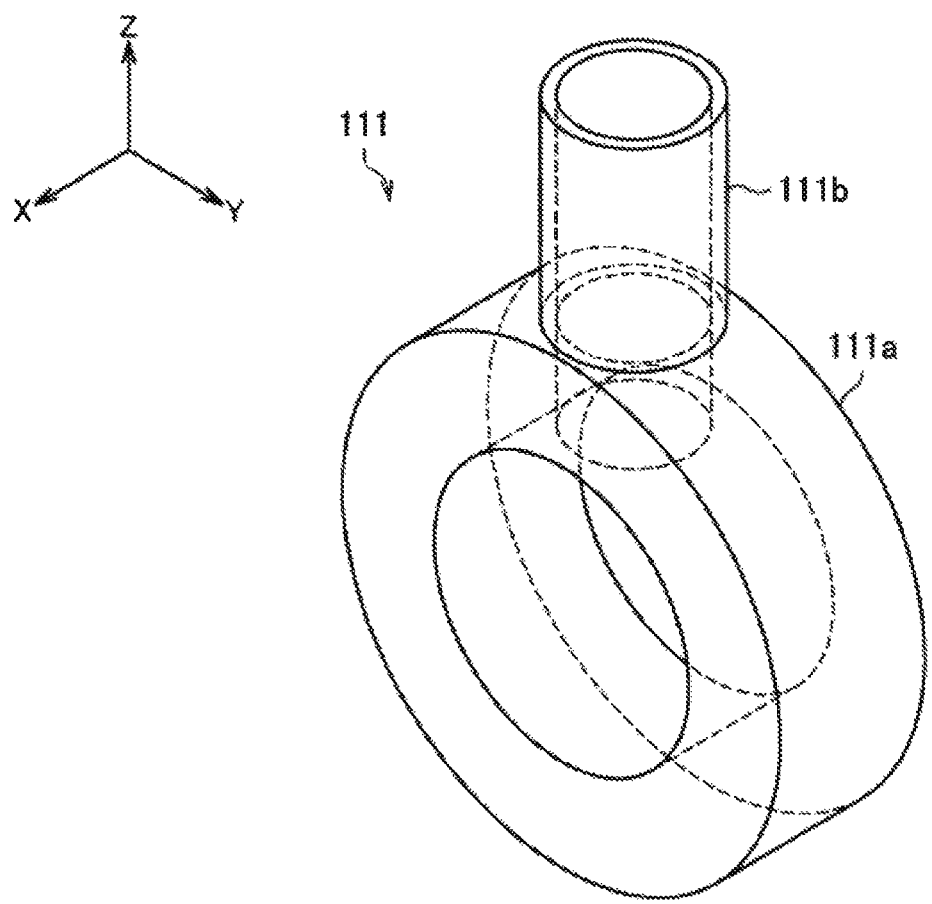

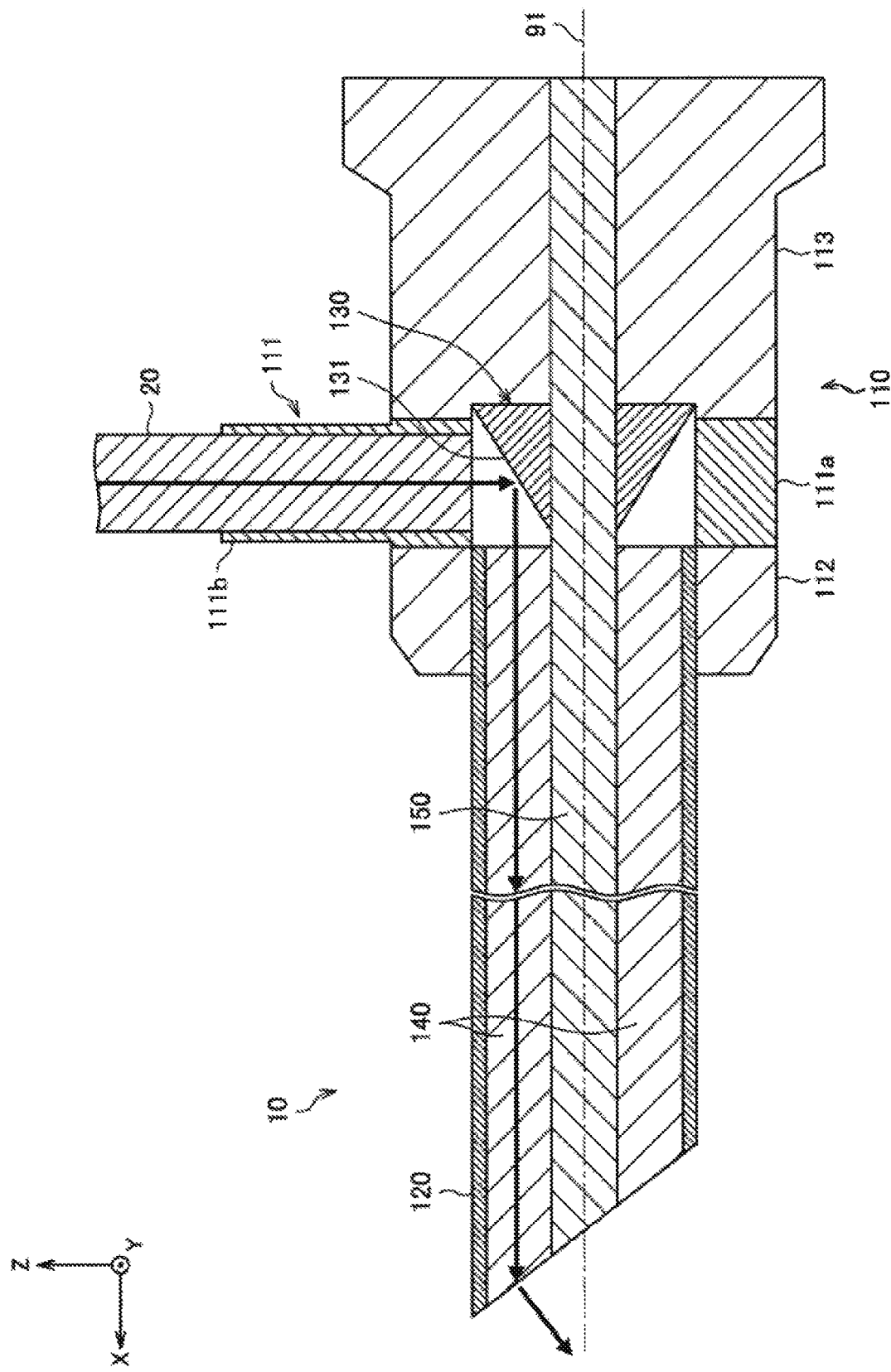

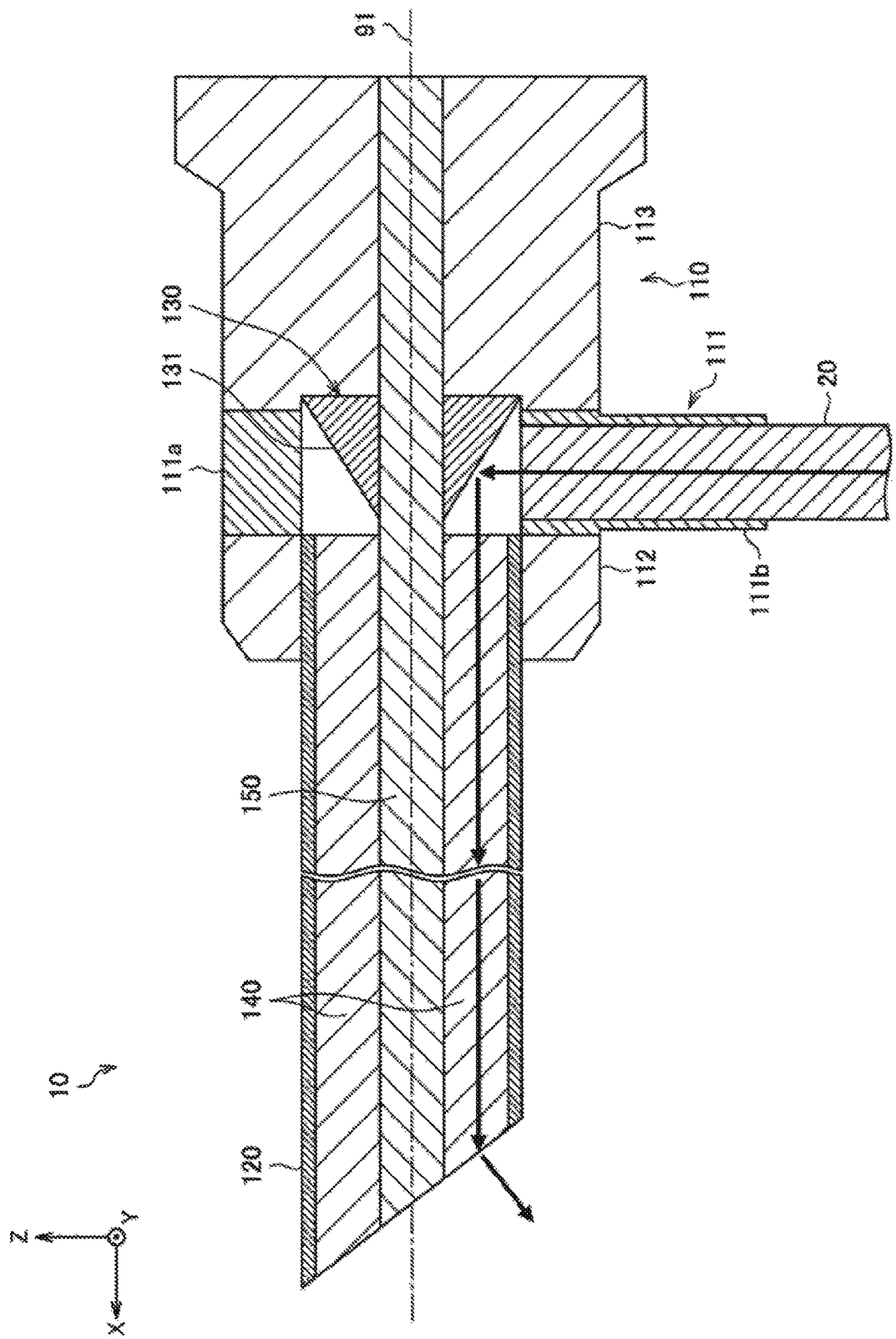
[FIG. 5]

[FIG. 6]
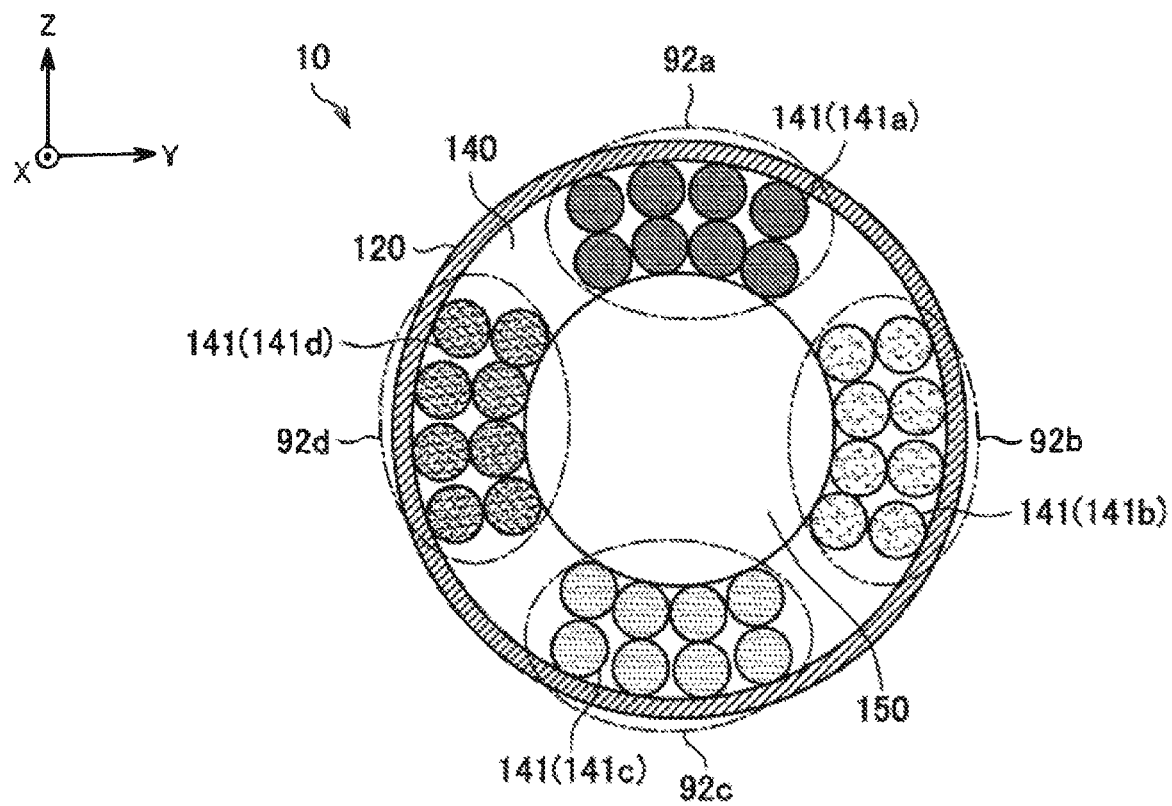
[FIG. 7]
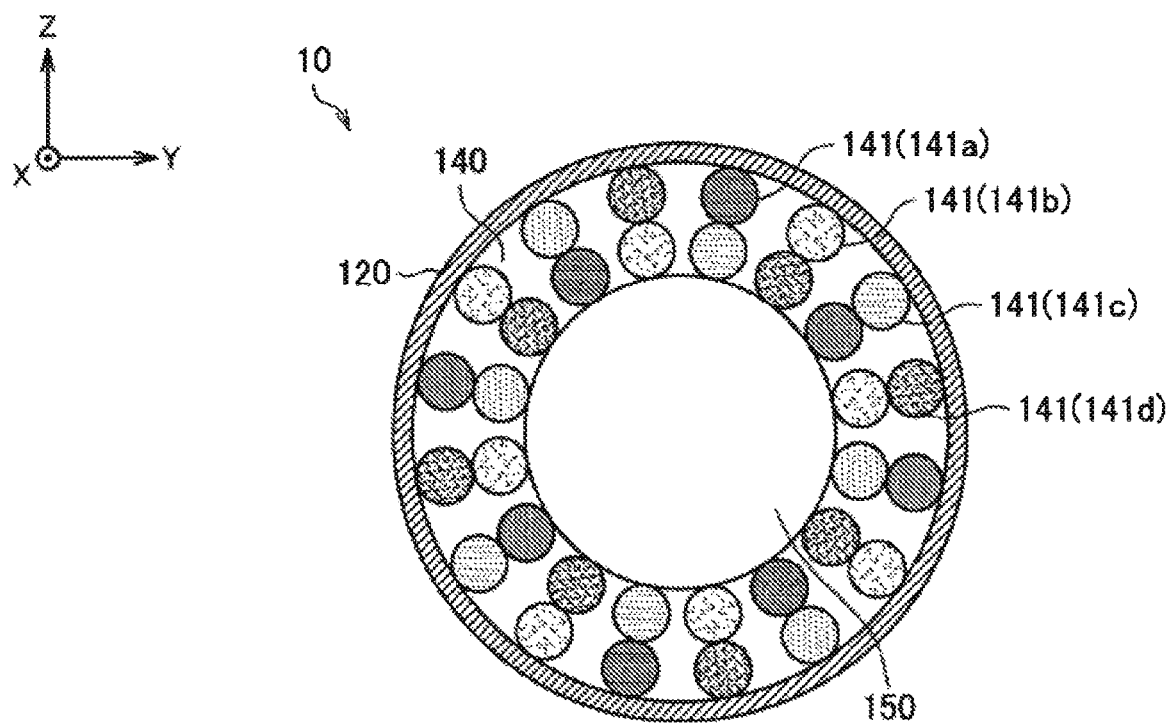

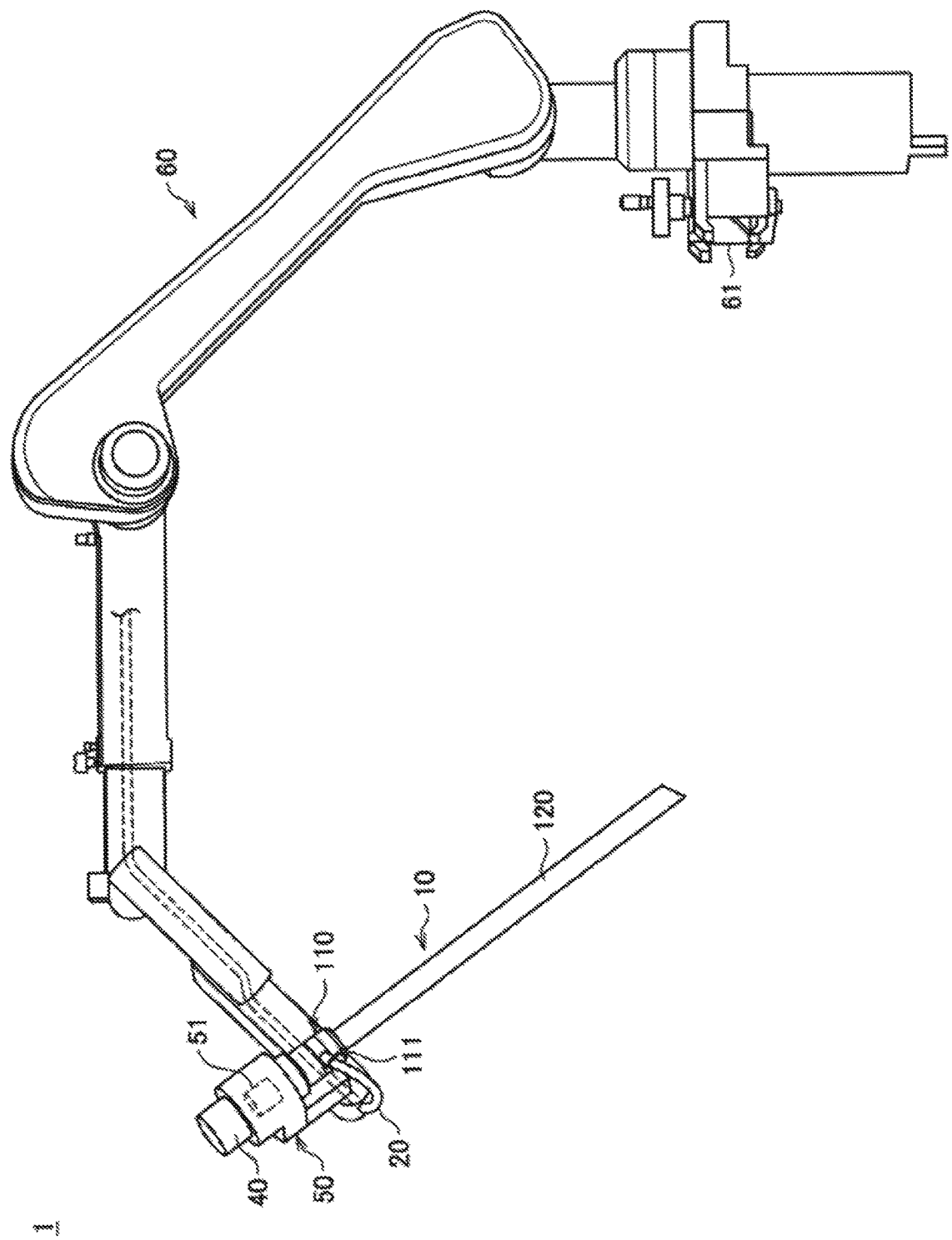
[FIG. 8]

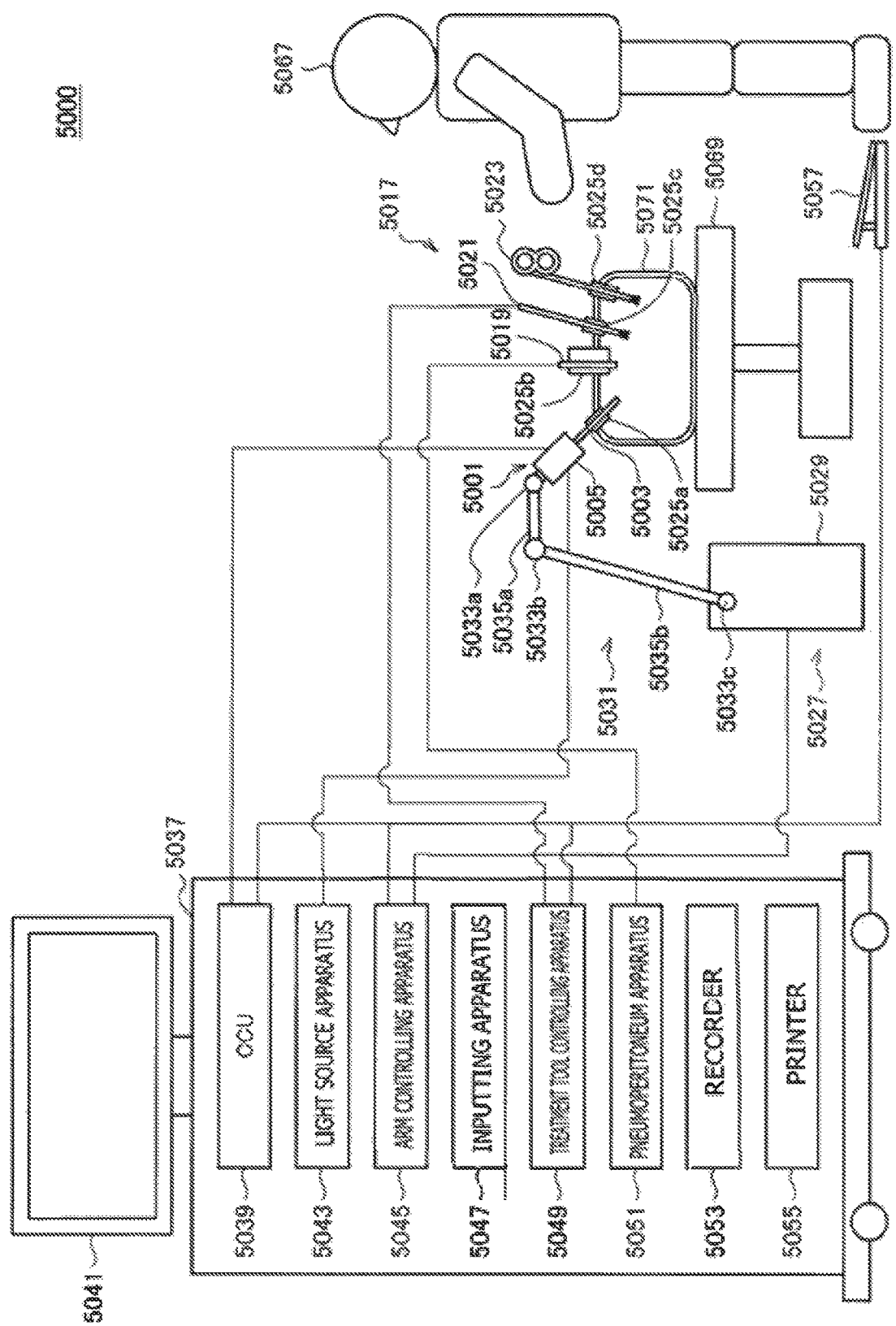

[FIG. 10]
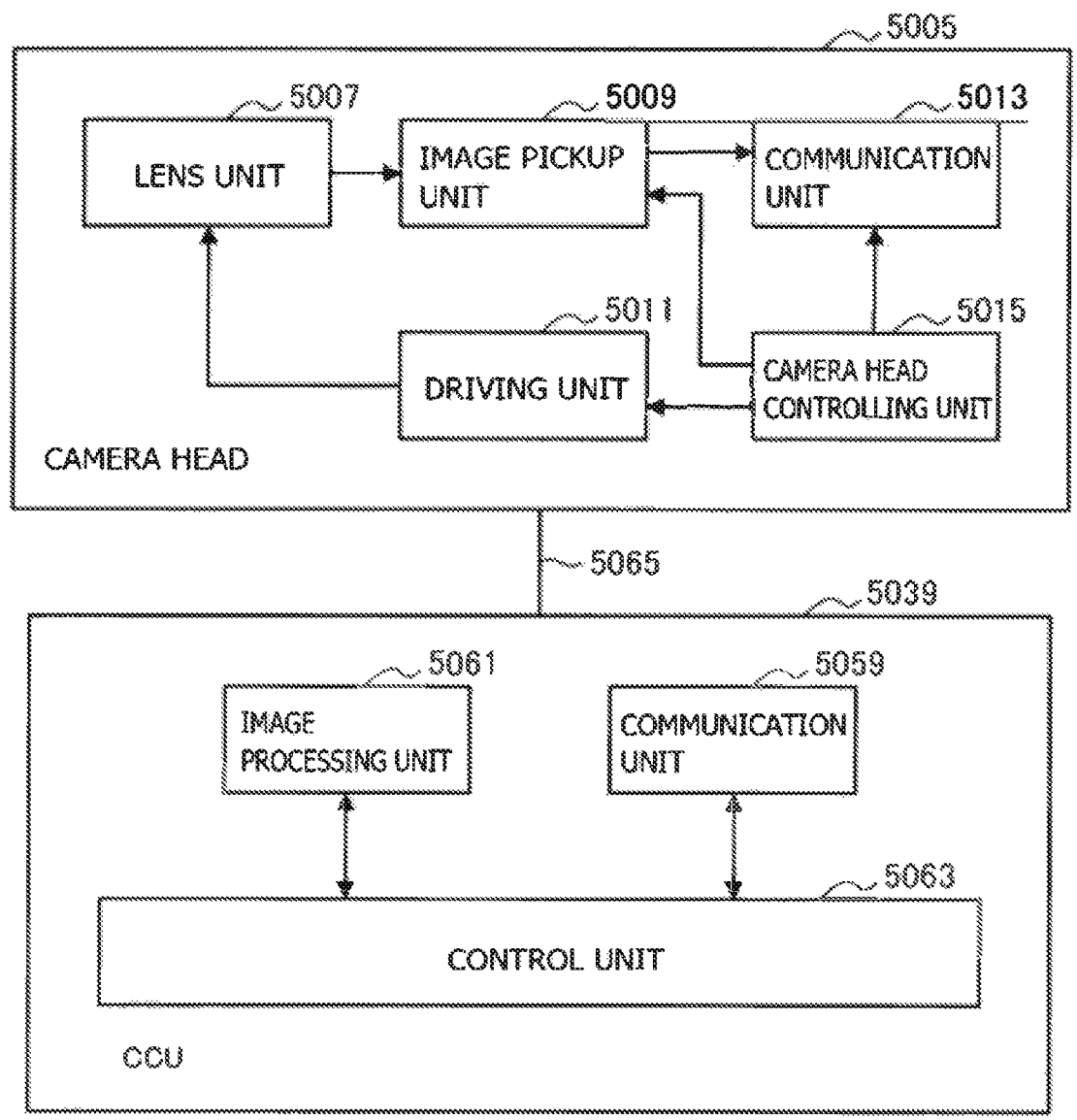

ENDOSCOPE AND ARM SYSTEM

CROSS REFERENCE TO RELATED APPLICATIONS

This application is a U.S. National Phase of International Patent Application No. PCT/JP2019/003917 filed on Feb. 4, 2019, which claims priority benefit of Japanese Patent Application No. JP 2018-052295 filed in the Japan Patent Office on Mar. 20, 2018. Each of the above-referenced applications is hereby incorporated herein by reference in its entirety.

TECHNICAL FIELD

The present disclosure relates to an endoscope and an arm system.

BACKGROUND ART

Endoscopes have been conventionally used in the medical field or the like to observe observation targets inside human bodies, for example. Specifically, some endoscopes each include, for example, a main body and a tubular section having a tubular form. The main body is attached to a camera head. The tubular section having a tubular form is fixed to the main body and extends from the main body. A subject is irradiated with light from the front-end portion of the tubular section. The subject is an observation target. The reflected light of the subject is captured by the front-end portion of the tubular section. Such an endoscope is used with a cable attached to the main body, for example, as disclosed in PTL 1. The cable is coupled to a light source.

CITATION LIST

Patent Literature

PTL 1: Japanese Unexamined Patent Application Publication No. 2003-279862

SUMMARY OF THE INVENTION

Problems to be Solved by the Invention

Incidentally, when observation is carried out by using an endoscope, the endoscope is sometimes rotated around the central axis of the tubular section. Specifically, when an oblique-viewing endoscope is used as the endoscope, a method is performed of rotating the oblique-viewing endoscope around the central axis of the tubular section, thereby allowing a desired field of view to be obtained. The method is called oblique-viewing endoscope rotation. When the endoscope is rotated in this way, the conventional technology has difficulty in appropriately rotating the endoscope. For example, in a case where the endoscope is rotated, a cable attached to the main body rotates along with the endoscope. This sometimes causes the cable to interfere with or be entwined with a nearby object, lowering the operability of the endoscope.

Accordingly, the present disclosure proposes a novel and improved endoscope and arm system each of which makes it possible to appropriately rotate the endoscope.

Means for Solving the Problems

According to the present disclosure, there is provided an endoscope including: a main body including a coupler to which a cable is attached; a tubular section having a tubular form; a reflector having a reflection surface that reflects light introduced from the coupler to inside of the main body and introduces the light to inside of the tubular section; a first optical system that transmits the light introduced by the reflector to the inside of the tubular section to a front-end portion of the tubular section and irradiates a subject with the light from the front-end portion; and a second optical system that transmits reflected light of the subject from the front-end portion of the tubular section to the main body side. The coupler is provided to be rotatable in the main body around a central axis of the tubular section with respect to another portion. The cable being coupled to a light source. The tubular section is fixed to the main body and extends from the main body.

In addition, according to the present disclosure, there is provided an arm system including: an endoscope; a camera head that captures a subject image obtained by the endoscope; a holding apparatus including an actuator; and a supporting arm having the holding apparatus installed at a front end. The actuator rotates the endoscope with respect to the camera head. The endoscope includes a main body including a coupler to which a cable is attached, a tubular section having a tubular form, a reflector having a reflection surface that reflects light introduced from the coupler to inside of the main body and introduces the light to inside of the tubular section, a first optical system that transmits the light introduced by the reflector to the inside of the tubular section to a front-end portion of the tubular section and irradiates a subject with the light from the front-end portion, and a second optical system that transmits reflected light of the subject from the front-end portion of the tubular section to the main body side. The coupler is provided to be rotatable in the main body around a central axis of the tubular section with respect to another portion. The cable is coupled to a light source. The tubular section is fixed to the main body and extends from the main body.

Effects of the Invention

As described above, according to the present disclosure, it is possible to appropriately rotate the endoscope.

It is to be noted that the above-described effects are not necessarily limitative. With or in the place of the above-described effects, there may be achieved any one of the effects described in this specification or other effects that may be grasped from this specification.

BRIEF DESCRIPTION OF DRAWING

FIG. 1 is a schematic diagram illustrating appearance of an endoscope according to an embodiment of the present disclosure.

FIG. 2 is a cross-sectional view of a schematic configuration of inside of the endoscope according to the embodiment.

FIG. 3 is a perspective view of a coupler according to the embodiment.

FIG. 4 is a schematic diagram illustrating a path of light in the endoscope in a case where a second cylindrical section faces a positive direction side of a Z direction.

FIG. 5 is a schematic diagram illustrating the path of the light in the endoscope in a case where the second cylindrical section faces a negative direction side of the Z direction.

FIG. 6 is a cross-sectional view of a schematic configuration of inside of a tubular section taken along a cross section passing a back-end portion of a first optical system according to the embodiment.

FIG. 7 is a cross-sectional view of the schematic configuration of the inside of the tubular section taken along a cross section passing a front-end portion of the first optical system according to the embodiment.

FIG. 8 is a schematic diagram illustrating a schematic configuration of an arm system to which the endoscope according to the embodiment is applied.

FIG. 9 is a view depicting an example of a schematic configuration of an endoscopic surgery system.

FIG. 10 is a block diagram depicting an example of a functional configuration of a camera head and a camera control unit (CCU) depicted in FIG. 9.

MODES FOR CARRYING OUT THE INVENTION

The following describes a preferred embodiment of the present disclosure in detail with reference to the accompanying drawings. It is to be noted that, in this specification and the accompanying drawings, components that have substantially the same functional configuration are indicated by the same reference signs and redundant description thereof is thus omitted.

It is to be noted that description is given in the following order.
1. Configuration of Endoscope
2. Operation of Endoscope
3. Effects of Endoscope
4. Arm System
5. Application Example
6. Conclusion

1. CONFIGURATION OF ENDOSCOPE

The configuration of an endoscope 10 according to an embodiment of the present disclosure is described with reference to FIG. 1 to FIG. 3. It is to be noted that FIG. 1 and FIG. 7 referred to below each illustrate the axial direction of a tubular section 120 as an X direction and the respective orthogonal directions of the radial direction of the tubular section 120 as a Y direction and a Z direction. Each of X-Y-Z coordinate systems illustrated in FIG. 1 to FIG. 7 is a coordinate system fixed for the tubular section 120. In addition, the following also refers to the tubular section 120 side (positive direction side in the X direction) with respect to a main body 110 as front end side and the main body 110 side (negative direction side in the X direction) with respect to the tubular section 120 as back end side.

FIG. 1 is a schematic diagram illustrating the appearance of the endoscope 10 according to the present embodiment. FIG. 2 is a cross-sectional view of the schematic configuration of the inside of the endoscope 10 according to the present embodiment. FIG. 3 is a perspective view of a coupler 111 according to the present embodiment.

Specifically, the endoscope 10 may be an oblique-viewing endoscope. When observation is carried out by using the endoscope 10 like this, oblique-viewing endoscope rotation is performed that rotates the endoscope 10 around a central axis 91 the tubular section 120 of the endoscope 10 to obtain a desired field of view. The endoscope 10 is used, for example, in the medical field to observe an observation target inside a human body. It is to be noted that the endoscope 10 may also be used in another field. For example, the endoscope 10 may also be used in the industrial field to observe the structure of the inside (especially where parts are incorporated in a complicated manner) of a machine.

As illustrated in FIG. 1, a cable 20 is attached to the endoscope 10. The cable 20 is coupled to a light source 30. The endoscope 10 irradiates a subject with light supplied from the light source 30 via the cable 20. The subject is an observation target. The endoscope 10 captures the reflected light of the subject to form a subject image.

Specifically, as illustrated in FIG. 1 and FIG. 2, the endoscope 10 includes the main body 110, the tubular section 120, a reflector 130, a first optical system 140, and a second optical system 150. The main body 110 includes the coupler 111 to which the cable 20 is attached. The cable 20 is coupled to the light source 30.

The main body 110 has, for example, a substantially circular column shape and is provided with an eyepiece on the back-end portion. The reflected light of the subject captured by the endoscope 10 is transmitted to the eyepiece. The eyepiece is not illustrated. For example, the main body 110 is coupled to a camera head. The camera head captures a subject image.

Specifically, as illustrated in FIG. 2, the main body 110 includes a first housing 112, the coupler 111, and a second housing 113. The first housing 112, the coupler 111, and the second housing 113 are disposed in this order from the front end side. The first housing 112 has a substantially annular shape. The back-end portion of the tubular section 120 is fitted to the inner circumferential portion of the first housing 112 for fixation. It is to be noted that the details of the coupler 111 are described below.

The tubular section 120 is fixed to the main body 110 and extends from the main body 110. Specifically, the tubular section 120 is fitted to the inner circumferential portion of the first housing 112 of the main body 110 for fixation. The tubular section 120 has a hollow tubular shape. Specifically, the tubular section 120 has a cylindrical shape. The endoscope 10 irradiates a subject with light from the front-end portion of the tubular section 120. The reflected light of the subject is captured by the front-end portion of the tubular section 120. Here, the front-end portion of the tubular section 120 is inclined with respect to the axial direction X. Light is emitted from the front-end portion of the tubular section 120 in the direction inclined with respect to the axial direction X. This makes it possible to observe a subject positioned with respect to the front-end portion of the tubular section 120 in the direction inclined with respect to the axial direction X.

It is to be noted that the transmission of light in the endoscope 10 is achieved by the coupler 111, reflector 130, first optical system 140, and second optical system 150 described below. Specifically, the second optical system 150 extends on the central axis 91 of the tubular section 120 from the front-end portion of the tubular section 120 to the back-end portion of the main body 110 as described below. In addition, specifically, the first optical system 140 is formed between the inner circumferential portion of the tubular section 120 and the second optical system 150.

The cable 20 is attached to the coupler 111 of the main body 110. The cable 20 is coupled to the light source 30. Light from the light source 30 is introduced from the coupler 111 to the inside of the main body 110. Here, in the present embodiment, the coupler 111 is provided to be rotatable in the main body 110 around the central axis 91 of the tubular section 120 with respect to another portion. This suppresses the cable 20 rotating along with the endoscope 10 when the endoscope 10 is rotated. Specifically, the coupler 111 is rotatable by 360° or more in the main body 110 with respect to another portion.

Specifically, as illustrated in FIG. 2 and FIG. 3, the coupler 111 includes a first cylindrical section 111a and a second cylindrical section 111b.

The first cylindrical section 111a has a cylindrical shape. The first cylindrical section 111a is disposed coaxially with the first housing 112 and the second housing 113 between these housings. Specifically, the front-end surface of the first cylindrical section 111a slidably comes into contact with the back-end surface of the first housing 112. The back-end surface of the first cylindrical section 111a slidably comes into contact with the front-end surface of the second housing 113. For example, the first cylindrical section 111a is then supported and guided by the first housing 112 and the second housing 113 to be rotatable around the central axis 91 of the tubular section 120.

The second cylindrical section 111b has a cylindrical shape. The second cylindrical section 111b extends outward in the radial direction of the first cylindrical section 111a from the side of the first cylindrical section 111a. The second cylindrical section 111b is formed to allow for communication between the internal space of the second cylindrical section 111b and the internal space of the first cylindrical section 111a. An end of the cable 20 is fitted to the second cylindrical section 111b from the outside of the endoscope 10 for attachment. This causes light from the light source 30 to be introduced from the coupler 111 to the inside of the main body 110 via the cable 20.

Here, the second cylindrical section 111b, to which an end of the cable 20 is attached, extends along the radial direction of the tubular section 120. In addition, the reflector 130 is disposed inside the first cylindrical section 111a. Specifically, this causes light from the light source 30 to be introduced to the reflector 130 from the coupler 111 along the direction (specifically, the radial direction of the tubular section 120) crossing the central axis 91 of the tubular section 120.

The reflector 130 has a reflection surface 131 that reflects light introduced from the coupler 111 to the inside of the main body 110 and introduces the light to the inside of the tubular section 120.

Specifically, the reflector 130 is provided in parallel with the back-end portion of the tubular section 120. More specifically, the reflector 130 is disposed inside the first cylindrical section 111a of the coupler 111 as described above. For example, the reflector 130 is fixed to the front-end surface of the second housing 113. Here, the reflector 130 is formed to cover the second optical system 150. This allows the reflector 130 to be provided while avoiding interference between the reflector 130 and the second optical system 150.

In addition, the reflection surface 131 of the reflector 130 has a truncated cone surface shape coaxial with the central axis 91 of the tubular section 120. Specifically, the reflector 130 has a shape obtained by forming a through hole on the central axis of a cone shape with a vertex on the positive direction side of the X direction. The reflector 130 has a mirror surface. The outside surface of the reflector 130 like this corresponds to the reflection surface 131. Light introduced from the coupler 111 to the reflector 130 along the direction crossing the central axis 91 of the tubular section 120 is therefore reflected by the reflection surface 131 to the back-end portion of the first optical system 140.

The first optical system 140 transmits light introduced by the reflector 130 to the inside of the tubular section 120 to the front-end portion of the tubular section 120 and irradiates a subject with the light from the front-end portion. Specifically, the first optical system 140 is formed between the inner circumferential portion of the tubular section 120 and the second optical system 150 as described above. In addition, specifically, the first optical system 140 includes a plurality of optical fibers extending from the back-end portion to the front-end portion of the first optical system 140. This allows light introduced from the reflector 130 to be transmitted to the front-end portion of the tubular section 120. It is to be noted that the details of the path of an optical fiber in the first optical system 140 are described below.

The second optical system 150 transmits the reflected light of a subject from the front-end portion of the tubular section 120 to the main body 110 side. Specifically, the second optical system 150 extends on the central axis 91 from the front-end portion of the tubular section 120 to the back-end portion of the main body 110 as described above. In addition, specifically, the second optical system 150 includes a plurality of lenses disposed at intervals along the axial direction X of the tubular section 120. This allows the front-end portion of the tubular section 120 to capture the reflected light of the subject to transmit the reflected light to the main body 110 side.

2. OPERATION OF ENDOSCOPE

Next, the operation of the endoscope 10 according to the present embodiment is described with reference to FIG. 4 to FIG. 7.

The path of light in the endoscope 10 is described first with reference to FIG. 4 and FIG. 5. The light is supplied from the light source 30. It is to be noted that FIG. 4 and FIG. 5 each illustrate the path of light supplied from the light source 30 as a thick arrow.

As described above, the coupler 111 is provided to be rotatable in the main body 110 around the central axis 91 of the tubular section 120 with respect to another portion. The coupler 111 may therefore have a different posture (specifically, the posture of the coupler 111 with respect to a portion other than the coupler 111 in the endoscope 10) in the endoscope 10. This may cause light to be introduced from the cable 20 to a different position in the endoscope 10. Even in a case where light is introduced from the cable 20 to a different position in the endoscope 10 according to the present embodiment in this way, the endoscope 10 is able to appropriately transmit the light. This allows an observation target to be appropriately observed.

FIG. 4 is a schematic diagram illustrating the path of light in the endoscope 10 in a case where the second cylindrical section 111b faces the positive direction side of the Z direction.

For example, in a case where the second cylindrical section 111b of the coupler 111 faces the positive direction side of the Z direction as illustrated in FIG. 4, the end of the cable 20 attached to the coupler 111 is positioned on the positive direction side of the Z direction. This causes light from the light source 30 to be introduced to a part of the reflection surface 131 of the reflector 130 on the positive direction side of the Z direction via the cable 20. The light introduced to the reflector 130 is then reflected by the reflection surface 131 to a part of the back-end portion of the first optical system 140 on the positive direction side of the Z direction. The first optical system 140 then transmits the light introduced to the part of the back-end portion of the first optical system 140 on the positive direction side of the Z direction to the front-end portion of the tubular section 120. The first optical system 140 irradiates a subject with the light.

FIG. 5 is a schematic diagram illustrating the path of light in the endoscope 10 in a case where the second cylindrical section 111*b* faces the negative direction side of the Z direction.

As described above, the coupler 111 rotates with respect to another portion of the main body 110. This may cause the coupler 111 to have a different posture in the endoscope 10. FIG. 5 corresponds to an example in which the coupler 111 has a different posture in the endoscope 10 from that of FIG. 4.

For example, in a case where the second cylindrical section 111*b* of the coupler 111 faces the negative direction side of the Z direction as illustrated in FIG. 5, the end of the cable 20 attached to the coupler 111 is positioned on the negative direction side of the Z direction. This causes light from the light source 30 to be introduced to a part of the reflection surface 131 of the reflector 130 on the negative direction side of the Z direction via the cable 20. The light introduced to the reflector 130 is then reflected by the reflection surface 131 to a part of the back-end portion of the first optical system 140 on the negative direction side of the Z direction. The first optical system 140 then transmits the light introduced to the part of the back-end portion of the first optical system 140 on the negative direction side of the Z direction to the front-end portion of the tubular section 120. The first optical system 140 irradiates a subject with the light.

Even in a case where the coupler 111 has any posture in the endoscope 10 as described above, the endoscope 10 is able to appropriately transmit light from the light source 30 to the front-end portion of the tubular section 120 and irradiate a subject with the light.

The path of an optical fiber is described here in detail with reference to FIG. 6 and FIG. 7. The path of an optical fiber defines the transmission path of light in the first optical system 140.

Specifically, the first optical system 140 includes a plurality of optical fibers extending from the back-end portion to the front-end portion of the first optical system 140 as described above. This causes light introduced to the back-end portion of the first optical system 140 to be transmitted to the front-end portion of the tubular section 120 through an optical fiber. The transmission path of light in the first optical system 140 is defined in this way by the path of an optical fiber in the first optical system 140.

The path of an optical fiber in the first optical system 140 is not particularly limited, but may be set in a variety of ways. It is, however, preferable to appropriately set the path of an optical fiber from the perspective of the stable irradiation of a subject with light from the front-end portion of the tubular section 120. Specifically, it is preferable to set the paths of optical fibers in the first optical system 140 to cause pieces of light emitted from the front-end portion of the tubular section 120 to have uniform distribution in the circumferential direction of the tubular section 120. The examples illustrated in FIG. 6 and FIG. 7 each correspond to an example of the path of an optical fiber set in this way in the first optical system 140.

FIG. 6 is a cross-sectional view of the schematic configuration of the inside of the tubular section 120 taken along a cross section passing the back-end portion of the first optical system 140 according to the present embodiment. Specifically, FIG. 6 illustrates the schematic configuration of the inside of the tubular section 120 taken along the A-A cross section in FIG. 2.

FIG. 6 illustrates a plurality of regions 92*a*, 92*b*, 92*c*, and 92*d* obtained by partitioning the first optical system 140 at the back-end portion of the first optical system 140 along the circumferential direction of the tubular section 120. The region 92*a* corresponds to a region at the back-end portion of the first optical system 140 on the positive direction side of the Z direction. The region 92*b* corresponds to a region at the back-end portion of the first optical system 140 on the positive direction side of the Y direction. The region 92*c* corresponds to a region at the back-end portion of the first optical system 140 on the negative direction side of the Z direction. The region 92*d* corresponds to a region at the back-end portion of the first optical system 140 on the negative direction side of the Y direction.

In addition, FIG. 6 applies the same type of hatching to optical fibers 141 positioned in the same region at the back-end portion of the first optical system 140 and applies different types of hatching to the optical fibers 141 positioned in different regions at the back-end portion of the first optical system 140. It is to be noted that, in a case where the following distinguishes the optical fibers 141 positioned in the regions 92*a*, 92*b*, 92*c*, and 92*d* from each other, the following refers to the optical fibers 141 positioned in the respective regions as optical fibers 141*a*, 141*b*, 141*c*, and 141*d*.

FIG. 7 is a cross-sectional view of the schematic configuration of the inside of the tubular section 120 taken along a cross section passing the front-end portion of the first optical system 140 according to the present embodiment. Specifically, FIG. 7 illustrates the schematic configuration of the inside of the tubular section 120 taken along the B-B cross section in FIG. 2.

As illustrated in FIG. 7, the optical fibers 141 positioned in the same region of a plurality of regions are disposed apart from each other in the circumferential direction of the tubular section 120 at the front-end portion of the first optical system 140. The plurality of regions is obtained by partitioning the first optical system 140 at the back-end portion of the first optical system 140 along the circumferential direction of the tubular section 120. For example, the optical fibers 141*a* positioned in the region 92*a* at the back-end portion of the first optical system 140 are disposed apart from each other in the circumferential direction of the tubular section 120 at the front-end portion of the first optical system 140. Similarly, the optical fibers 141*b*, 141*c*, and 141*d* respectively positioned in the regions 92*b*, 92*c*, and 92*d* at the back-end portion of the first optical system 140 are disposed apart from each other in the circumferential direction of the tubular section 120 at the front-end portion of the first optical system 140. The disposition of the optical fibers 141 like this may be achieved, for example, by the spiral paths of the respective optical fibers 141 in the first optical system 140 around the central axis 91 of the tubular section 120.

Here, as described with reference to FIG. 4 and FIG. 5, the endoscope 10 introduces light reflected by the reflection surface 131 to a portion of the regions at the back-end portion of the first optical system 140. For example, in the example illustrated in FIG. 4, light reflected by the reflection surface 131 is introduced chiefly to the region 92*a* positioned on the positive direction side of the Z direction at the back-end portion of the first optical system 140 and transmitted chiefly by the optical fiber 141*a*. In addition, for example, in the example illustrated in FIG. 5, light reflected by the reflection surface 131 is introduced chiefly to the region 92c positioned on the negative direction side of the Z direction at the back-end portion of the first optical system 140 and transmitted chiefly by the optical fiber 141c.

In a case where each of the optical fibers 141 extends in the X direction in the first optical system 140, the optical fibers 141 positioned in the same region at the back-end portion of the first optical system 140 are not disposed apart from each other in the circumferential direction of the tubular section 120, but are disposed in proximity even at the front-end portion of the first optical system 140. This causes pieces of light reflected by the reflection surface 131 to be transmitted by the first optical system 140. The pieces of light are then emitted to a subject from positions at the front-end portion of the tubular section 120 that are unevenly distributed in the circumferential direction. Further, different positions are irradiated with pieces of light at the front-end portion of the tubular section 120 in accordance with the posture of the coupler 111 in the endoscope 10.

In contrast, in a case where the optical fibers 141 positioned in the same region at the back-end portion of the first optical system 140 are disposed apart from each other in the circumferential direction of the tubular section 120 at the front-end portion of the first optical system 140, pieces of light are uniformly emitted to positions in the circumferential direction of the tubular section 120 at the front-end portion of the tubular section 120 regardless of regions to which the pieces of light are introduced at the back-end portion of the first optical system 140. This allows pieces of light emitted from the front-end portion of the tubular section 120 to have uniform distribution in the circumferential direction of the tubular section 120 regardless of the posture of the coupler 111 in the endoscope 10. It is therefore possible to stably irradiate a subject with light from the front-end portion of the tubular section 120.

As described above, the first optical system 140 preferably transmits light reflected from the reflection surface 131 of the reflector 130 to the front-end portion of the tubular section 120 to cause pieces of light emitted from the front-end portion to have uniform distribution in the circumferential direction of the tubular section 120. Specifically, as described with reference to FIG. 6 and FIG. 7, it is preferable that the optical fibers 141 positioned in the same region of a plurality of regions be disposed apart from each other in the circumferential direction of the tubular section 120 at the front-end portion of the first optical system 140. The plurality of regions is obtained by partitioning the first optical system 140 at the back-end portion of the first optical system 140 along the circumferential direction of the tubular section 120.

3. EFFECTS OF ENDOSCOPE

Next, effects of the endoscope 10 according to the present embodiment are described.

In the endoscope 10 according to the present embodiment, the coupler 111 is provided to be rotatable (specifically, rotatable by 360° or more) in the main body 110 around the central axis 91 of the tubular section 120 with respect to another portion. The cable 20 is attached to the coupler 111. The cable 20 is coupled to the light source 30. In addition, the reflector 130 is provided that has the reflection surface 131 which reflects light introduced from the coupler 111 to the inside of the main body 110 and introduces the light to the inside of the tubular section 120. This makes it possible to transmit light from the light source 30 to the front-end portion of the tubular section 120 regardless of the posture of the coupler 111 in the endoscope 10 and irradiate a subject with the light while suppressing the cable 20 rotating along with the endoscope 10 when rotating the endoscope 10.

The endoscope 10 according to the present embodiment is able to suppress the cable 20 rotating along with the endoscope 10 in this way when rotating the endoscope 10, making it possible to attain a variety of effects.

For example, it is possible to suppress the cable 20 interfering with or being entwined with a nearby object. This allows the operability of the endoscope 10 to be increased. In addition, for example, it is possible to suppress the rotation of the cable 20 imposing a load on the endoscope 10 because of the gravity or tension caused by the cable 20. This allows the operability of the endoscope 10 to be increased. In addition, for example, in a case where the endoscope 10 is used for the medical field, it is possible to suppress the contamination of a surgical region of a patient by the cable 20 coming into the surgical region because of the movement of the cable 20 in the unexpected direction. In addition, it is easier to handle the cable 20. This eliminates the possibility of even the rotational operation of the endoscope 10 interrupting a surgical operation.

In addition, it is possible to rotates the endoscope 10 by 360° or more independently from the cable 20. This makes it easier to control the rotation of the endoscope 10, for example, in a case where the rotation of the endoscope 10 is controlled by a control apparatus. In addition, for example, in a case where the endoscope 10 is rotated while being supported by a supporting arm as described below, it is possible to suppress the cable 20 and the coupler 111 interfering with the supporting arm or the like. In addition, it is possible in that case to fix the cable 20 to the supporting arm. This allows the degree of freedom for disposing the cable 20 to be increased.

As described above, the endoscope 10 according to the present embodiment makes it possible to appropriately rotate the endoscope 10.

In addition, in the endoscope 10 according to the present embodiment, the second optical system 150 may extend on the central axis 91 of the tubular section 120 from the front-end portion to the back-end portion of the tubular section 120. The back-end portion of the tubular section 120 is the end on the side opposite to the tubular section 120 in the main body 110. In addition, the first optical system 140 may be formed between the inner circumferential portion of the tubular section 120 and the second optical system 150. In addition, light from the light source 30 may be introduced from the coupler 111 to the reflector 130 along the direction crossing the central axis 91. In addition, the reflector 130 may be provided in parallel with the back-end portion and formed to cover the second optical system 150. The back-end portion is the end of the tubular section 120 on the main body 110 side. In addition, the reflection surface 131 of the reflector 130 has a truncated cone surface shape coaxial with the central axis 91. The reflection surface 131 of the reflector 130 may reflect light to the back-end portion that is the end of the first optical system 140 on the main body 110 side. The light is introduced from the coupler 111 to the inside of the main body 110. The endoscope has the above-described configuration, thereby making it possible to appropriately achieve the transmission of light from the light source 30 to the front-end portion of the tubular section 120 regardless of the posture of the coupler 111 in the endoscope 10 and the irradiation of a subject with the light while suppressing the cable 20 rotating along with the endoscope 10 when rotating the endoscope 10.

In addition, in the endoscope 10 according to the present embodiment, the first optical system 140 may transmit light reflected from the reflection surface 131 of the reflector 130 to the front-end portion of the tubular section 120 to cause pieces of light emitted from the front-end portion to have uniform distribution in the circumferential direction of the tubular section 120. This makes it possible to suppress the emission of the pieces of light reflected by the reflection surface 131 to a subject from positions at the front-end portion of the tubular section 120 that are unevenly distributed in the circumferential direction after transmission by the first optical system 140. It is therefore possible to stably irradiate a subject with light from the front-end portion of the tubular section 120.

In addition, in the endoscope 10 according to the present embodiment, the first optical system 140 may include the plurality of optical fibers 141 extending from the back-end portion to the front-end portion. The back-end portion is the end of the first optical system 140 on the main body 110 side. The front-end portion is the end of the first optical system 140 on the side opposite to the main body 110. In addition, the optical fibers 141 positioned in the same region of a plurality of regions are disposed apart from each other in the circumferential direction of the tubular section 120 at the front-end portion of the first optical system 140. The plurality of regions is obtained by partitioning the first optical system 140 at the back-end portion of the first optical system 140 along the circumferential direction of the tubular section 120. The back-end portion of the first optical system 140 is the end of the first optical system 140 on the main body 110 side. The front-end portion of the first optical system 140 is the end of the first optical system 140 on the side opposite to the main body 110. This makes it possible to appropriately achieve the uniform distribution of pieces of light emitted from the front-end portion of the tubular section 120 in the circumferential direction of the tubular section 120 regardless of the posture of the coupler 111 in the endoscope 10. It is therefore possible to appropriately achieve the stable irradiation of a subject with light from the front-end portion of the tubular section 120.

4. ARM SYSTEM

Next, an arm system 1 to which the endoscope 10 according to the present embodiment is applied is described with reference to FIG. 8.

FIG. 8 is a schematic diagram illustrating the schematic configuration of the arm system 1 to which the endoscope 10 according to the present embodiment is applied.

The arm system 1 is an example of an arm system mounted with the above-described endoscope 10. Specifically, the arm system 1 is used in the medical field to observe an observation target inside a human body by using the endoscope 10. It is to be noted that the arm system 1 may also be used in another field. For example, the arm system 1 may also be used in the industrial field to observe the structure of the inside (especially where parts are incorporated in a complicated manner) of a machine by using the endoscope 10.

Specifically, as illustrated in FIG. 8, the arm system 1 includes the endoscope 10, a camera head 40, a holding apparatus 50, and a supporting arm 60.

The supporting arm 60 includes a clamp section 61 for attaching the supporting arm 60 to an operating bed. The supporting arm 60 is attached to the operating bed via the clamp section 61. Specifically, the supporting arm 60 includes a plurality of joint sections and a plurality of link sections. The posture of the supporting arm 60 is controlled by the control apparatus that is not illustrated, thereby controlling the position and posture of the endoscope 10 supported by the front-end portion of the supporting arm 60.

The holding apparatus 50 is installed at the front-end portion of the supporting arm 60 and holds the endoscope 10. Specifically, the main body 110 of the endoscope 10 is held by the holding apparatus 50. In addition, the holding apparatus 50 holds the camera head 40 on the side opposite to the endoscope 10. That is, the holding apparatus 50 has a function of holding the endoscope 10 and the camera head 40 to couple the endoscope 10 and the camera head 40. At the front-end portion of the supporting arm 60, the endoscope 10, the holding apparatus 50, and the camera head 40 are disposed in this order.

The camera head 40 has a function of capturing a subject image obtained by the endoscope 10.

Here, in the arm system 1, the holding apparatus 50 includes an actuator 51 that rotates the endoscope 10 with respect to the camera head 40. Specifically, a portion other than the coupler 111 in the endoscope 10 is rotated by the actuator 51. This allows the camera head 40 to capture an image having a desired field of view. It is to be noted that the operation of the actuator 51 is controlled by the control apparatus which is not illustrated.

It is to be noted that the holding apparatus 50 specifically includes an actuator for a camera in addition to the actuator 51 that rotates the endoscope 10. The actuator for a camera is an actuator that rotates the camera head 40 with respect to the endoscope 10. Driving the actuator for a camera to rotate the camera head 40 with respect to the endoscope 10 on the basis of the posture of the supporting arm 60 makes it possible to maintain a constant direction as the direction of gravity in an image captured by the camera head 40 regardless of the posture of the supporting arm 60. It is to be noted that the actuator for a camera may be omitted from the components of the holding apparatus 50. In that case, for example, a weight may be coupled to the camera head 40 directly or via another member and the posture of the camera head 40 may be adjusted by using the gravity caused by the weight to keep a constant direction as the direction of gravity in an image captured by the camera head 40 regardless of the posture of the supporting arm 60.

As described above, in the endoscope 10, the coupler 111 is provided to be rotatable (specifically, rotatable by 360° or more) in the main body 110 around the central axis 91 of the tubular section 120 with respect to another portion. The cable 20 is attached to the coupler 111. The cable 20 is coupled to the light source 30. In addition, the reflector 130 is provided that has the reflection surface 131 which reflects light introduced from the coupler 111 to the inside of the main body 110 and introduces the light to the inside of the tubular section 120. This makes it possible to transmit light from the light source 30 to the front-end portion of the tubular section 120 regardless of the posture of the coupler 111 in the endoscope 10 and irradiate a subject with the light while suppressing the cable 20 rotating along with the endoscope 10 when rotating the endoscope 10.

The arm system 1 according to the present embodiment that is mounted with the endoscope 10 like this is able to suppress the cable 20 rotating along with the endoscope 10 when rotating the endoscope 10, making it possible to attain a variety of effects.

For example, it is possible to facilitate the rotation of the endoscope 10 caused by the actuator 51 to be controlled. In addition, for example, it is possible to suppress the cable 20 and the coupler 111 interfering with the supporting arm 60, the holding apparatus 50, and the camera head 40. The holding apparatus 50 and the camera head 40 are installed at the supporting arm 60. In addition, for example, it is possible to fix the cable 20 to the supporting arm 60. This allows the degree of freedom for disposing the cable 20 to be increased.

As described above, the arm system 1 according to the present embodiment makes it possible to appropriately rotate the endoscope 10.

Further, it is preferable that the supporting arm 60 be hollow and the cable 20 be housed in the internal space of the supporting arm 60 as illustrated in FIG. 8. It is to be noted that FIG. 8 uses a dashed line to partially illustrate an example of the path of the cable 20 in the internal space of the supporting arm 60. This makes it possible to more effectively suppress the cable 20 interfering with or being entwined with a nearby object. Further, the cable 20 is housed in the internal space of the supporting arm 60. This prevents the cable 20 from coming into contact with the floor. There is thus no possibility that the cable 20 is contaminated. This also helps keeping a clean region, which is of importance in an operating room. In addition, the cable 20 has a different posture, making it possible to suppress the center-of-gravity position of the supporting arm 60 from being changed. This makes it possible to facilitate the posture of the supporting arm 60 to be stably controlled.

5. APPLICATION EXAMPLE

The technology according to the present disclosure is applicable to a variety of products. For example, the technology according to the present disclosure may be applied to an endoscopic surgery system.

FIG. 9 is a view depicting an example of a schematic configuration of an endoscopic surgery system 5000 to which the technology according to an embodiment of the present disclosure can be applied. In FIG. 9, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025*a* to 5025*d* are used to puncture the abdominal wall. Then, a lens barrel 5003 of the endoscope 5001 and the other surgical tools 5017 are inserted into body cavity of the patient 5071 through the trocars 5025*a* to 5025*d*. In the example depicted, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033*a*, 5033*b* and 5033*c* and links 5035*a* and 5035*b* and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840 x vertical pixel number 2160), 8K (horizontal pixel number 7680 x vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy device 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 9, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endo scope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrow-band light and/or excitation light suitable for special light observation as described above.

(Camera Head and CCU)

Functions of the camera head 5005 of the endoscope 5001 and the CCU 5039 are described in more detail with reference to FIG. 10. FIG. 10 is a block diagram depicting an example of a functional configuration of the camera head 5005 and the CCU 5039 depicted in FIG. 9.

Referring to FIG. 10, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

The technology according to the present disclosure may be favorably applied to the endoscope 5001 and supporting arm apparatus 5027 of the above-described components. Specifically, the endoscope 10 described with reference to FIG. 1 to FIG. 7 is applicable as the endoscope 5001. The arm system 1 described with reference to FIG. 8 is applicable as the endoscope 5001 and supporting arm apparatus 5027. This allows the endoscope to be appropriately rotated. It is thus possible to attain a variety of effects such as increasing the operability of the endoscope, increasing the controllability of the rotation of the endoscope, avoiding the contamination of a surgical region, or increasing the degree of freedom for disposing the cable that is coupled to the light source.

6. CONCLUSION

As described above, in the endoscope 10 according to the present embodiment, the coupler 111 is provided to be rotatable (specifically, rotatable by 360° or more) in the main body 110 around the central axis 91 of the tubular section 120 with respect to another portion. The cable 20 is attached to the coupler 111. The cable 20 is coupled to the light source 30. In addition, the reflector 130 is provided that has the reflection surface 131 which reflects light introduced from the coupler 111 to the inside of the main body 110 and introduces the light to the inside of the tubular section 120. This makes it possible to transmit light from the light source 30 to the front-end portion of the tubular section 120 regardless of the posture of the coupler 111 in the endoscope 10 and irradiate a subject with the light while suppressing the cable 20 rotating along with the endoscope 10 when rotating the endoscope 10. This makes it possible to appropriately rotate the endoscope 10.

The preferred embodiment(s) of the present disclosure has/have been described above with reference to the accompanying drawings, whilst the present disclosure is not limited to the above examples. It is apparent that a person having ordinary skill in the art of the present disclosure may arrive at various alterations and modifications within the scope of the technical idea described in the appended claims and it is understood that such alterations and modifications naturally fall within the technical scope of the present disclosure.

Specifically, the shape and disposition of the respective components of the endoscope 10 are not limited to the examples described with reference to FIG. 1 to FIG. 3. For example, the shape of the main body 110 and the position at which the coupler 111 is provided to the main body 110 may be different from the above-described examples. In addition, the reflection surface 131 of the reflector 130 may have a different shape from the strict truncated cone shape. For example, the reflection surface 131 of the reflector 130 may have a shape obtained by combining a plurality of curved surfaces.

In addition, the above has described the example in which the coupler 111 is supported and guided by the first housing 112 and the second housing 113 to be rotatable around the central axis 91 of the tubular section 120, but the coupler 111 may be supported by another component. For example, the coupler 111 may be supported and guided by the reflector 130 to be rotatable around the central axis 91 of the tubular section 120.

In addition, the above has described the example in which the reflector 130 is fixed to a portion of the main body 110 other than the coupler 111 (specifically, the front-end surface of the second housing 113), but the reflector 130 may be fixed to the coupler 111. In that case, the reflector 130 is rotatable around the central axis 91 of the tubular section 120 integrally with the coupler 111.

In addition, the above has described the example in which the reflector 130 is a mirror, but the reflector 130 may be another optical member. It is sufficient if the reflector 130 has a reflection surface that reflects light introduced from the coupler 111 to the inside of the main body 110 and introduces the light to the inside of the tubular section 120. For example, the reflector 130 may be an optical member such as a beam splitter or a prism having a reflection surface.

In addition, the effects described herein are merely illustrative and exemplary, but not limitative. That is, the technology according to the present disclosure may exert other effects that are apparent to those skilled in the art from the description herein in addition to the above-described effects or in place of the above-described effects.

It is to be noted that the following configurations also fall within the technical scope of the present disclosure.

(1)

An endoscope including:
 a main body including a coupler to which a cable is attached, the cable being coupled to a light source;
 a tubular section having a tubular form, the tubular section being fixed to the main body and extending from the main body;
 a reflector having a reflection surface, the reflection surface reflecting light introduced from the coupler to inside of the main body and introducing the light to inside of the tubular section;
 a first optical system that transmits the light introduced by the reflector to the inside of the tubular section to a front-end portion of the tubular section and irradiates a subject with the light from the front-end portion; and
 a second optical system that transmits reflected light of the subject from the front-end portion of the tubular section to the main body side, in which
 the coupler is provided to be rotatable in the main body around a central axis of the tubular section with respect to another portion.

(2)
 The endoscope according to (1), in which
 the second optical system extends on the central axis from the front-end portion of the tubular section to an end of the main body on a side opposite to the tubular section, and
 the first optical system is formed between an inner circumferential portion of the tubular section and the second optical system.

(3)
 The endoscope according to (2), in which
 light from the light source is introduced from the coupler to the reflector along a direction crossing the central axis, and
 the reflector is provided in parallel with an end of the tubular section on the main body side and formed to cover the second optical system.

(4)
 The endoscope according to (3), in which the reflection surface of the reflector has a truncated cone surface shape coaxial with the central axis and reflects the light to an end of the first optical system on the main body side, the light being introduced from the coupler to the inside of the main body.

(5)
 The endoscope according to any one of (2) to (4), in which the first optical system transmits the light reflected from the reflection surface to the front-end portion to cause pieces of light emitted from the front-end portion of the tubular section to have uniform distribution in a circumferential direction of the tubular section.

(6)
 The endoscope according to (5), in which
 the first optical system includes a plurality of optical fibers extending from an end of the first optical system on the main body side to an end of the first optical system on a side opposite to the main body, and
 the optical fibers positioned in a same region of a plurality of regions are disposed apart from each other in the circumferential direction of the tubular section at the end of the first optical system on the side opposite to the main body, the plurality of regions being obtained by partitioning the first optical system along the circumferential direction of the tubular section at the end of the first optical system on the main body side.

(7)
 An arm system including:
 an endoscope;
 a camera head that captures a subject image obtained by the endoscope;
 a holding apparatus including an actuator, the actuator rotating the endoscope with respect to the camera head; and
 a supporting arm having the holding apparatus installed at a front end,
 the endoscope including
  a main body including a coupler to which a cable is attached, the cable being coupled to a light source,
  a tubular section having a tubular form, the tubular section being fixed to the main body and extending from the main body,
  a reflector having a reflection surface, the reflection surface reflecting light introduced from the coupler to inside of the main body and introducing the light to inside of the tubular section,
  a first optical system that transmits the light introduced by the reflector to the inside of the tubular section to a front-end portion of the tubular section and irradiates a subject with the light from the front-end portion, and
  a second optical system that transmits reflected light of the subject from the front-end portion of the tubular section to the main body side, in which
 the coupler is provided to be rotatable in the main body around a central axis of the tubular section with respect to another portion.

(8)
 The arm system according to (7), in which
 the supporting arm is hollow, and
 the cable is housed in an internal space of the supporting arm.

(9)
 The arm system according to (7) or (8), in which
 the second optical system extends on the central axis from the front-end portion of the tubular section to an end of the main body on a side opposite to the tubular section, and
 the first optical system is formed between an inner circumferential portion of the tubular section and the second optical system.

(10)
 The arm system according to (9), in which
 light from the light source is introduced from the coupler to the reflector along a direction crossing the central axis, and
 the reflector is provided in parallel with an end of the tubular section on the main body side and formed to cover the second optical system.

(11)
 The arm system according to (10), in which the reflection surface of the reflector has a truncated cone surface shape coaxial with the central axis and reflects the light to an end of the first optical system on the main body side, the light being introduced from the coupler to the inside of the main body.

(12)
 The medical arm system according to any one of (9) to (11), in which the first optical system transmits the light reflected from the reflection surface to the front-end portion to cause pieces of light emitted from the front-end portion of the tubular section to have uniform distribution in a circumferential direction of the tubular section.

(13) The arm system according to (12), in which
the first optical system includes a plurality of optical fibers extending from an end of the first optical system on the main body side to an end of the first optical system on a side opposite to the main body, and
the optical fibers positioned in a same region of a plurality of regions are disposed apart from each other in the circumferential direction of the tubular section at the end of the first optical system on the side opposite to the main body, the plurality of regions being obtained by partitioning the first optical system along the circumferential direction of the tubular section at the end of the first optical system on the main body side.

REFERENCE SIGNS LIST 1 arm system
endoscope
cable
light source
camera head
holding apparatus
actuator
supporting arm
clamp section
110 main body
111 coupler
111a first cylindrical section
111b second cylindrical section
112 first housing
113 second housing
120 tubular section
130 reflector
131 reflection surface
140 first optical system
141 optical fiber
150 second optical system

The invention claimed is:

1. An endoscope, comprising:
a main body including a coupler to which a cable is attached, wherein the cable is coupled to a light source;
a tubular section having a tubular form, wherein the tubular section is fixed to the main body and extends from the main body;
a reflector having a reflection surface, wherein the reflection surface is configured to reflect light introduced from the coupler to inside of the main body and introduce the light to inside of the tubular section;
a first optical system comprising at least one optical fiber, wherein the first optical system is configured to transmit the light introduced by the reflector to the inside of the tubular section to a front-end portion of the tubular section and irradiate a subject with the light from the front-end portion; and
a second optical system comprising at least one lens, wherein the second optical system is configured to transmit reflected light of the subject from the front-end portion of the tubular section to the main body, wherein the coupler is rotatable in the main body around a central axis of the tubular section with respect to another portion of the main body.

2. The endoscope according to claim 1, wherein
the second optical system extends on the central axis from the front-end portion of the tubular section to an end of the main body on a side opposite to the tubular section, and the first optical system is between an inner circumferential portion of the tubular section and the second optical system.

3. The endoscope according to claim 2, wherein
the coupler is configured to introduce light from the light source to the reflector along a direction crossing the central axis, and
the reflector is in parallel with an end of the tubular section on a side of the main body and covers the second optical system.

4. The endoscope according to claim 3, wherein
the reflection surface of the reflector has a truncated cone surface shape coaxial with the central axis,
the reflection surface is further configured to reflect the light to an end of the first optical system on the side of the main body, and
the light is introduced from the coupler to the inside of the main body.

5. The endoscope according to claim 2, wherein the first optical system is further configured to transmit the light reflected from the reflection surface to the front-end portion to cause pieces of light emitted from the front-end portion of the tubular section to have uniform distribution in a circumferential direction of the tubular section.

6. The endoscope according to claim 5, wherein
the first optical system includes a plurality of optical fibers, including the at least one optical fiber, extending from an end of the first optical system on a side of the main body to an end of the first optical system on a side opposite to the main body,
the plurality of optical fibers positioned in a same region of a plurality of regions are disposed apart from one another in the circumferential direction of the tubular section at the end of the first optical system on the side opposite to the main body, and
the plurality of regions is obtained by partitioning the first optical system along the circumferential direction of the tubular section at the end of the first optical system on the side of the main body.

7. An arm system, comprising:
an endoscope;
a camera head configured to capture a subject image obtained by the endoscope;
a holding apparatus including an actuator, wherein the actuator is configured to rotate the endoscope with respect to the camera head; and
a supporting arm having the holding apparatus installed at a front end of the supporting arm, wherein the endoscope includes:
a main body including a coupler to which a cable is attached, wherein the cable is coupled to a light source;
a tubular section having a tubular form, wherein the tubular section is fixed to the main body and extends from the main body;
a reflector having a reflection surface, wherein the reflection surface is configured to reflect light introduced from the coupler to inside of the main body and introduce the light to inside of the tubular section;
a first optical system comprising at least one optical fiber, wherein the first optical system is configured to transmit the light introduced by the reflector to the inside of the tubular section to a front-end portion of the tubular section and irradiate a subject with the light from the front-end portion; and a second optical system comprising at least one lens,
wherein the second optical system is configured to transmit reflected light of the subject from the front-end portion of the tubular section to the main body,
wherein the coupler is rotatable in the main body around a central axis of the tubular section with respect to another portion of the main body.

8. The arm system according to claim 7, wherein
the supporting arm is hollow, and
the cable is housed in an internal space of the supporting arm.

9. The arm system according to claim 7, wherein
the second optical system extends on the central axis from the front-end portion of the tubular section to an end of the main body on a side opposite to the tubular section, and
the first optical system is between an inner circumferential portion of the tubular section and the second optical system.

10. The arm system according to claim 9, wherein
the coupler is configured to introduce light from the light source to the reflector along a direction crossing the central axis, and
the reflector is in parallel with an end of the tubular section on a side of the main body and covers the second optical system.

11. The arm system according to claim 10, wherein
the reflection surface of the reflector has a truncated cone surface shape coaxial with the central axis,
the reflection surface is further configured to reflect the light to an end of the first optical system on the side of the main body, and
the light is introduced from the coupler to the inside of the main body.

12. The arm system according to claim 9, wherein the first optical system is further configured to transmit the light reflected from the reflection surface to the front-end portion to cause pieces of light emitted from the front-end portion of the tubular section to have uniform distribution in a circumferential direction of the tubular section.

13. The arm system according to claim 12, wherein
the first optical system includes a plurality of optical fibers, including the at least one optical fiber, extending from an end of the first optical system on a side of the main body to an end of the first optical system on a side opposite to the main body,
the plurality of optical fibers positioned in a same region of a plurality of regions are disposed apart from one another in the circumferential direction of the tubular section at the end of the first optical system on the side opposite to the main body, and
the plurality of regions is obtained by partitioning the first optical system along the circumferential direction of the tubular section at the end of the first optical system on the side of the main body.

* * * * *